United States Patent [19]

Matsuda et al.

[11] Patent Number: 6,075,066
[45] Date of Patent: Jun. 13, 2000

[54] MATERIAL TO BE WORN ON THE EYEBALL

[75] Inventors: Takehisa Matsuda; Hiroshi Nakao, both of Osaka, Japan

[73] Assignee: Seikagaku Kogyo Kabushiki Kaisha, Tokyo, Japan

[21] Appl. No.: 08/869,983

[22] Filed: Jun. 5, 1997

Related U.S. Application Data

[63] Continuation of application No. 08/549,722, filed as application No. PCT/JP95/00419, Mar. 14, 1995, abandoned.

[30] Foreign Application Priority Data

Mar. 14, 1994 [JP] Japan .................................. 6-068147

[51] Int. Cl.[7] ...................................................... G02B 1/04
[52] U.S. Cl. ......................... 523/106; 536/55.1; 536/55.2; 351/160 H; 264/1.7
[58] Field of Search ........................ 523/106; 351/160 H; 536/55.1, 55.2; 264/1.7

[56] References Cited

U.S. PATENT DOCUMENTS

| 4,223,984 | 9/1980 | Miyata et al. ....................... 351/160 H |
| 4,260,228 | 4/1981 | Miyata ................................ 351/160 H |
| 4,264,155 | 4/1981 | Miyata ................................ 351/160 H |
| 4,447,562 | 5/1984 | Ivani ........................................ 523/106 |
| 4,886,350 | 12/1989 | Wichterle ........................... 351/160 H |
| 5,044,742 | 9/1991 | Cohen ................................. 351/160 H |
| 5,487,895 | 1/1996 | Dapper et al. .......................... 424/484 |

FOREIGN PATENT DOCUMENTS

| 0 486 294 A2 | 5/1992 | European Pat. Off. .......... C08L 5/08 |
| 56-94322 | 7/1981 | Japan ................................ G02C 7/04 |
| 62-42487 | 9/1987 | Japan ................................ G02C 7/04 |
| 63-50816 | 3/1988 | Japan ................................ G02C 7/04 |
| 4-176459 | 6/1992 | Japan ................................ A61F 9/04 |
| 5-163384 | 6/1993 | Japan ................................ C08L 5/00 |
| 5-313105 | 11/1993 | Japan ................................ G02C 7/04 |

OTHER PUBLICATIONS

Hiroshi Nakao et al., Folia Ophthalmologica Japonica, 45(5), 484–489 (1994) Month? International Search Report.

J.P.F. Strachan, "Further Comments on the Fitting of Spherical Hydrophilic Lenses . . . ," *The Australian Journal of Optometry*, 1975, pp. 11–22.

*Primary Examiner*—Andrew E. C. Merriam
*Attorney, Agent, or Firm*—Sughrue, Mion, Zinn, Macpeak & Seas, PLLC

[57] ABSTRACT

The present invention provides semi-spherical materials to be worn on the eyeball, such as contact lenses for visual acuity correction or medical treatment use, cornea protecting materials, controlled drug release contact lenses and the like, which comprise, as a main component, a glycosaminoglycan existing in the living body as an extracellular matrix component of connective tissues and satisfy various requirements such as dimentional stability, transparency, surface water wettability, tissue compatibility, oxygen permeability and the like. In other words, the material to be worn on the eyeball has a shape of semi-spherical surface compatible in shape with the mammalian eyeball and has biological and surface-physical compatibilities with ophthalmic tissues and comprises, as a main component, a substantially transparent photocured crosslinked-glycosaminoglycan obtained by allowing photoreactive groups covalently bonded to a glycosaminoglycan to crosslink mutually by photoirradiation.

13 Claims, 1 Drawing Sheet

MATERIAL TO BE WORN ON THE EYEBALL

This is a Continuation of application Ser. No. 08/549,722 filed Mar. 1, 1996, now abandoned, which was filed as PCT/JP95/00419 on Mar. 14, 1990.

TECHNICAL FIELD

This invention relates to materials to be worn on the eyeball comprising a photocured crosslinked-glycosaminoglycans, particularly to a material to be worn on the eyeball which is transparent and has a shape of semi-spherical surface with excellent dimensional stability (shape stability) and high surface wettability.

BACKGROUND ART

Contact lenses (to be referred to as "CL" hereinafter) are roughly divided into hard contact lenses (to be referred to as "HCL" hereinafter) and soft contact lenses (to be referred to as "SCL" hereinafter) depending on the flexibility of raw materials. The conventional HCL raw materials cannot be applied to continuous wearing for a prolonged period of time because of their impermeability of oxygen which is necessary for the metabolism of corneal tissues. Hence, raw materials having high oxygen permeability have been developed and are now popularly applied to continuously wearable HCL having high oxygen permeability. With regard to the raw materials of SCL, on the other hand, hydrous high polymers having high oxygen permeability have been used and are now popularly applied to continuously wearable highly hydrous SCL. However, since the contact time of the CL material with ophthalmic tissues such as cornea, conjunctiva and the like becomes long as the continuous wearing of CL is prolonged, it has been desired to develop a material having more high tissue compatibility (biocompatibility with ophthalmic tissues).

Collagen has been known as a CL material having tissue compatibility (JP-B 62-42487, U.S. Pat. No. 4,223,984, U.S. Pat. No. 4,260,228, U.S. Pat. No. 4,264,155) and commercialized as Collagen Lens (Bausch & Lomb, U.S.A.) (the term "JP-B" as used herein means an "examined Japanese patent publication"). Also, JP-B 62-42487 discloses a CL which is formed after mixing collagen with a chondroitin sulfate or the like mucopolysaccharide (glycosaminoglycan). However, collagen, which is a protein, has a disadvantage of having antigenicity. The eye is highly sensitive especially against exogeneous material and apt to cause inflammations when the exogeneous material has antigenicity.

In addition, various raw materials of the CL and the like materials to be worn on the eyeball have been known, such as a raw material which comprises a polyvinyl alcohol-based gel containing a chondroitin sulfate or the like acid polysaccharide (JP-B 51-11139), chitin or chitosan (JP-A 56-94322, JP-W 61-501729, JP-A 63-50816, JP-A 4-176459, JP-A 4-275346 and the like), glucomannan (JP-A 5-163384), silk fibroin (JP-A 5-313105) and the like (the term "JP-A" as used herein means an "unexamined published Japanese patent application", and the term "JP-W" as used herein means an "unexamined published Japanese international patent application"). However, all of such raw materials have a problem in terms of tissue compatibility, because their principal components do not originate from biological materials(vertebrate).

As described above, raw CL materials which contain glycosaminoglycan are known, but no CL which substantially comprises glycosaminoglycan alone.

An object of the present invention is to provide materials to be worn on the eyeball having a semi-spherical shape, such as contact lenses for use in the visual acuity correction or medical treatment, cornea-protecting materials (corneal bandages) or controlled drug release contact lenses, which comprise, as their main component, a glycosaminoglycan (mucopolysaccharide) existing in the living body as an extracellular matrix component of connective tissues and the like, and satisfy various requirements such as dimentional stability, transparency, surface wettability, tissue compatibility (non-irritation, safety), oxygen permeability and the like.

DISCLOSURE OF THE INVENTION

The present invention relates to (1) a material to be worn on the eyeball having a shape of semi-spherical surface compatible in shape with the mammalian eyeball and having biological and surface-physical compatibilities with ophthalmic tissues, which comprises, as a main component, a substantially transparent photocured crosslinked-glycosaminoglycan obtained by allowing photoreactive groups covalently bonded to a glycosaminoglycan to crosslink by photoirradiation.

Its preferred embodiments include:

(2) the material to be worn on the eyeball according to the above embodiment (1) wherein the photoreactive groups covalently bonded to the glycosaminoglycan are acyl groups of cinnamic acid or a derivative thereof, 1-carboxyalkylthymine or 7-coumaryloxyacetic acid;

(3) the material to be worn on the eyeball according to the above embodiment (1) wherein the glycosaminoglycan is hyaluronic acid or chondroitin sulfate;

(4) the material to be worn on the eyeball according to the above embodiment (1) wherein the material surface has high water wettability;

(5) the material to be worn on the eyeball according to the above embodiment (4) wherein the water wettability of material surface is defined to be about 20 to 50° as receding contact angle with water;

(6) the material to be worn on the eyeball according to the above embodiment (1) wherein the material has percent optical transmittance of about 90% or more at a wave length of 550 nm;

(7) the material to be worn on the eyeball according to the above embodiment (1) wherein gelation ratio of the photocured crosslinked-glycosaminoglycan is about 50% or more;

(8) the material to be worn on the eyeball according to the above embodiment (1) wherein gelation ratio of the photocured crosslinked-glycosaminoglycan is about 80% or more;

(9) the material to be worn on the eyeball according to the above embodiment (1) wherein the material has a characteristic as a contact lens for use in visual acuity correction;

(10) the material to be worn on the eyeball according to the above embodiment (1) wherein diameter of the material is about 5 to 20 mm, and the base curve of the material is about 6 to 9 mm.

(11) the material to be worn on the eyeball according to the above embodiment (1) wherein the range of linear swelling ratio of the material is approximately from 1 to 40%.

(12) the material to be worn on the eyeball according to the above embodiment (1) wherein the range of refractive index of the material is about 1.3 to 1.6.

(13) the material to be worn on the eyeball according to the above embodiment (1) wherein the photocured crosslinked-glycosaminoglycan has a multilayer structure having different crosslinking densities.

(14) the material to be worn on the eyeball wherein said material in the above embodiment (1) has water wettability of material surface as receding contact angle with water of about 20 to 50°, has percent optical transmittance of about 90% or more at a wave length of 550 nm and a refractive index of about 1.3 to 1.6, and has gelation ratio of the photocured crosslinked-glycosaminoglycan being about 50% or more.

(15) Use of a substantially transparent photocured crosslinked-glycosaminoglycan, which is obtained by allowing photoreactive groups covalently bonded to a glycosaminoglycan to crosslink mutually by irradiation, for manufacture of a material to be worn on the eyeball having a shape of semi-spherical surface. compatible in shape with the mammalian eyeball and having biological and surface-physical compatibilities.

(16) Use according to the above embodiment (15), wherein the material to be worn on the eyeball is a contact lens for use in visual acuity correction.

The term "material to be worn on the eyeball" as used herein basically means a semi-spherical surface body compatible in shape with the eyeball, or having a proper radius of curvature. More precisely, it is a member for use in the visual acuity correction and/or medical treatment, which has such a transparency that it does not obstruct the field of vision and has such a shape and a size that it can closely cover at least most of the corneal portion of the eyeball (front surface of the eye) and can be kept on the front surface of the eye by mediation of tear fluid, or has such a semilunar, falciform or elliptic curved surface body and a size that it can be kept on the surface of the eye by inserting it inside the lower eyelid. The materials include those which are generally called contact lenses for visual acuity correction use, contact lenses for medical treatment use, cornea-protecting materials (corneal bandages), controlled drug release contact lenses and the like. As a consequence, the material of the present invention to be worn on the eyeball has a shape of a semi-spherical surface compatible in shape with the eyeball, and it means not only a shape resulting from the cutting of a part of a spherical surface but also those on which holes, notches or slots are partly arranged.

In addition, though the material of the present invention to be worn on the eyeball is basically constructed from a photocured crosslinked-glycosaminoglycan, it may further contain various substances depending on the purpose, which include, for example, a physiologically active compound, a pigment (preferably a natural pigment), a dye and a structural protein such as collagen, keratin, elastin or the like.

[Photocured crosslinked-glycosaminoglycan]

The photocured crosslinked-glycosaminoglycan to be used as the main component of the material of the present invention to be worn on the eyeball is a compound substantially insoluble in water and organic solvents, which is obtained by irradiating a light (preferably an ultraviolet ray having a wavelength of approximately 260 to 400 nm, more preferably about 290 to 400 nm) to a glycosaminoglycan having photoreactive groups covalently bonded thereto (to be referred to as "photoreactive group-bonded glycosaminoglycan" hereinafter) to effect dimerization of the photoreactive groups and resulting crosslinking of glycosaminoglycan chains (cf. EP-A2-0554898; *J. Am. Soc. Artif. Intern. Organs*, 38, 154–157, 1992; and *Jinko Zoki* (Artificial Organs), 22(2), 376–379, 1993).

The term "glycosaminoglycan" as used herein means a group of acid polysaccharides, each having a repeating unit of disaccharide consisting of an amino sugar and uronic acid (or galactose), which are also known as mucopolysaccharides. Its illustrative examples include hyaluronic acid (to be referred to as "HA" hereinafter), chondroitin sulfate (to be referred to as "CS" hereinafter), chondroitin, dermatan sulfate, heparin, heparan sulfate, keratan sulfate and the like. HA and CS are preferable for the purpose of the present invention taking account of cost, availability and the like. HA may have an average molecular weight of preferably from about 50,000 to 3,500,000, more preferably from about 600,000 to 3,000,000. CS may have an average molecular weight of preferably from about 1,000 to 100,000, more preferably from about 20,000 to 80,000. As to the CS, the kinds of molecules of chondroitin sulfate A (chondroition 4-sulfate), chondroitin sulfate C (chondroition 6-sulfate), chondroitin sulfate D, chondroitin E, chondroitin sulfate K, and the like are known, and used in the present invention as a glycosaminoglycan. Chondroitin sulfate A and chondroitin C are most preferable for the cost, availability and the like.

Though various substituent groups capable of undergoing photodimerization reaction can be used as the photoreactive groups, acyl groups originated from cinnamic acid or derivatives thereof, 1-carboxyalkylthymines or 7-coumaryloxyacetic acid are preferable taking biocompatibility, safety, cost and the like into consideration. Illustrative examples of the cinnamic acid derivatives include those which have a lower alkyl group having preferably 1–6 carbon atoms (e.g.; methyl or ethyl for example), a lower alkoxyl group having preferably 1–6 carbon atoms (e.g.; methoxyl or ethoxyl for example), nitro group, amino group or the like substituent on the benzene ring. An example of the 1-carboxyalkylthymine is 1-(2-carboxyethyl) thymine. The photoreactive group which gives most suitable physical properties for the purpose of the present invention is a cinnamoyl group which is an acyl group originated from cinnamic acid.

When the photoreactive group is an acyl group, its covalent bonding with a glycosaminoglycan is an ester bonding between a hydroxyl group of the glycosaminoglycan and the acyl group. The ester bonding reaction can be effected by allowing the acyl group-containing acid anhydride or acid halide (acyl chloride or the like) to react with the hydroxyl group of the glycosaminoglycan as an organic solvent-soluble salt (for example, tri-n-butylamine salt, triethylamine salt or pyridine salt) of the glycosaminoglycan in an organic solvent such as dimethylformamide (DMF), dimethyl sulfoxide (DMSO), hexamethyl phosphoramide (HMPA), tetrahydrofuran (THF), dioxane, N-methyl-2-pyrrolidone or the like in the presence of a base such as pyridine, or as a water-soluble salt (sodium salt for example) of the glycosaminoglycan in an aqueous solvent (water (preferably purified water), buffer solution (e.g.; phosphate buffer, carbonate buffer or the like for example)) in the presence of a catalyst such as 4-dimethylaminopyridine, 4-pyrrolidinopyridine or the like and of a base such as triethylamine or sodium bicarbonate at 0° C. to 100° C., preferably 70° C. to 90° C., for several tens of minutes to several tens of hours, preferably 1 to 10 hours.

The degree of substitution (DS) of photoreactive groups to a glycosaminoglycan can be controlled as desired by controlling the reaction conditions.

The term "degree of substitution (DS)" of photoreactive groups as used herein is defined as the number of substituted photoreactive groups with hydroxyl groups per the disaccharide repeating unit of a glycosaminoglycan (in the case of HA, DS=4.0 when all hydroxyl groups are substituted). DS can be determined by H-NMR.

For example, the DS can be increased by increasing the mole ratio of an acid having the acyl group aforementioned, containing the photoreactive group or a reactive derivative thereof relative to the starting glycosaminoglycan and/or prolonging the reaction time.

The photoreactive group-bonded glycosaminoglycan thus obtained is recovered from the reaction mixture, and dissolved in an organic solvent (e.g. DMF, DMSO) or in an aqueous solvent (e.g. water (preferably purified water) and a buffer solution (e.g. phosphate buffer, carbonate buffer) prior to photocuring and crosslinking reaction.

After removing the solvent from the organic or aqueous solvent solution of the photoreactive group-bonded glycosaminoglycan to form a thin film, the film is exposed to a light to obtain a photocured crosslinked-glycosaminoglycan insolubilized by the photocuring and crosslinking reaction.

For example, a typical reaction scheme where the photoreactive group-bonded glycosaminoglycan is a cinnamic acid-bonded HA is shown below.

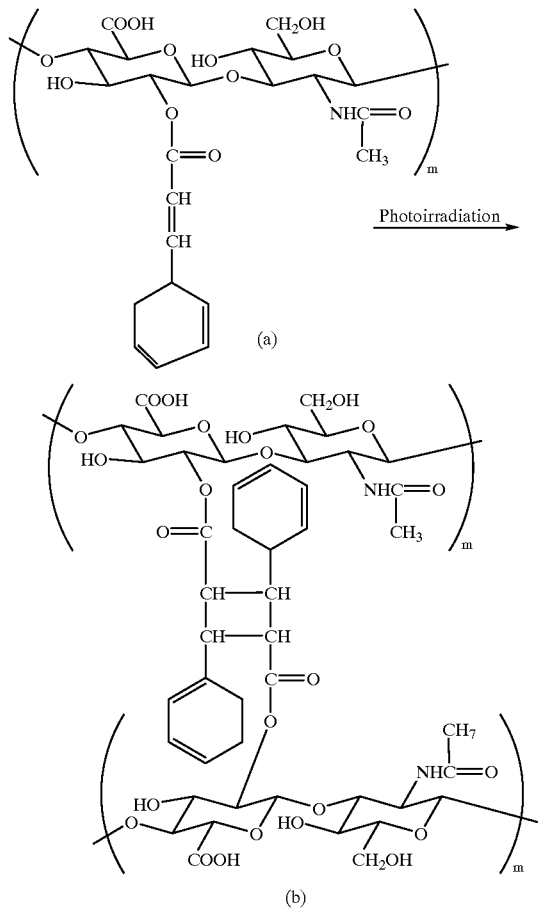

In the above formula, (a) represents cinnamic acid-bonded HA where the number of repeating units of HA is m, that is calculated from molecular weight of HA. Though the scheme showed the example of cinnamoyl group introduced into 2-hydroxyl group of uronic acid in order to simplify the scheme, the other hydroxyl groups other than the 2-hydroxyl group can be substituted with cinnamoyl group, and (b) indicates crosslinking completed by mutual photodimerization of cinnamoyl groups. In this instance, all of the repeating units do not have to be crosslinked, but the intermolecular crosslinking occurring at least between some molecules is sufficient. The dimerization reaction mechanism by the above photodimerizable group is common to any photoreactive group-containing glycosaminoglycans having other photocurable and crosslinkable groups.

As the degree of substitution (DS) of photoreactive groups to a glycosaminoglycan increases, the crosslinking density increases and the equilibrium water absorption decreases. As a result, in the case of cinnamic acid-bonded HA, for example, the glycosaminoglycan becomes a sol at a low degree of substitution (DS, 0.2 or less), a gel at an intermediate value (DS, 0.2 to 1.0) or a plastic having low water absorption coefficient at an even higher DS value.

The crosslinking density of photoreactive groups also varies depending on the irradiation time and intensity of light. In consequence, irradiation of light to a photoreactive group-containing glycosaminoglycan can be carried out by fixing and/or moving (including changes in the direction) the light source and/or the material to be irradiated. The irradiation can also be effected through a mold which will be described later.

For example, when a photocured crosslinked-HA having a gelation ratio of about 80% may be obtained by irradiating an ultraviolet light of 290 nm or more (irradiation intensity, 0.26 mW/cm$^2$) to a cinnamic acid-bonded HA resulting from the coupling of cinnamic acid-originated acyl groups with hydroxyl groups of HA, it is necessary to carry out the irradiation for 15 minutes or more when a cinnamic acid-bonded HA having a degree of substitution (DS) with cinnamic acid of 1.7 is used (the gelation ratio reaches about 85% after irradiation of about 30 minutes and hardly increases by further irradiation), and 5 minutes or more of irradiation is required when a cinnamic acid-bonded HA having a DS value of 2.9 is used (the gelation ratio reaches about 90% after irradiation of about 7 to 10 minutes and hardly increases by further irradiation). Also, a photocured crosslinked-HA having a gelation ratio of about 50 to 80% may be obtained by about 10 to 15 minutes of irradiation when a cinnamic acid-bonded HA having a DS value of 1.7 is used. The term "gelation ratio" as used herein means a value calculated by dividing the weight of the photocured crosslinked-glycosaminoglycan, which is measured after being washed with an organic solvent (DMF or the like) to remove the uncrosslinked glycosaminoglycan, by the weight of the photoreactive group-bonded glycosaminoglycan before crosslinking and multiplying the divided value by 100.

According to the present invention, an appropriate DS value, irradiation time and irradiation intensity are selected so as to give desired crosslink density and gelation ratio corresponding to various applications of the material to be worn on the eyeball (contact lenses for visual acuity correction use, contact lenses for medical treatment use, cornea protective materials, controlled drug release contact lenses and the like).

For example, when it is necessary to keep a constant shape for a relatively prolonged period of time like the case of contact lenses for visual acuity correction use, the material may preferably have a gelation ratio of about 80% or more and a DS value of 1.0 or more in the case of a cinnamic acid-bonded HA. Especially, when the DS value is about 1.5 or more, the resulting material to be worn on the eyeball is mechanically hard and excellent in surface water wettability, but its water content is low and its physical properties become close to those of commercial HCL articles. Therefore, preferable DS of HCL type is 1.0 to 4.0, more preferably 1.0 to 3.5. When the material is used for treatment purpose, like the case of contact lenses for medical treatment use, cornea protective materials and the like, expecting its corneal disease healing effect or cornea protective effect, the period of time-required for keeping its shape is relatively short (approximately 1 to 20 days) and such a material to be worn on the eyeball may have a gelation ratio of about 50% or more and a DS value of about 0.2 or more. When the DS value of the material is lower than about 1.0, its linear swelling ratio and oxygen permeability increase, but its strength and refractive index decrease, along with an increase of the water content. Therefore, preferable DS of SCL type is 0.1 to 1.0, more preferably 0.2 to 0.9.

When a physiologically active compound (to be described later) is further included in the material, it is desirable to mix the compound with a solution of the photoreactive group-bonded glycosaminoglycan prior to the photocuring and crosslinking reaction. Alternatively, after the photocuring and crosslinking reaction, the compound can be incorporated by impregnating the photocured crosslinked-glycosaminoglycan with a solution of the compound or by means of electrophoresis.

[Molding]

The material of the present invention to be worn on the eyeball can be molded by known CL molding methods (JP-W 61-501729, JP-A 63-50816, JP-A 5-93889) such as cut polishing, spin casting (centrifugal casting), pressing, molding and the like, of which spin casting is particularly preferred.

For example, the spin cast molding is carried out by preparing a mold 1 as shown in FIG. 1 (in the drawing, (a) is a sectional view of the mold along the line A—A, (b) is its perspective view and (c) is its overhead view), installing the mold in a spin coater, pouring an organic or aqueous solvent solution of a photoreactive group-bonded glycosaminoglycan into a depressed portion 3 shown and evaporating the solvent by rotation. Though not particularly limited, evaporation of the solvent may be effected by heating and/or under a reduced pressure. Diameter and base curve 2 of the material to be worn on the eyeball can be determined by the shape of the mold, namely the depressed portion 3, its thickness is determined by the concentration or viscosity of the photoreactive group-bonded glycosaminoglycan solution, and the ratio of the thickness of its central portion to that of its peripheral portion can be controlled by changing rotating speed of the mold.

The following table shows results of an examination on the changes in the thickness of a CL at various portions, which was prepared by subjecting a DMF solution of a cinnamic acid-bonded HA (100 mg/ml) having a DS value of 1.62 to spin casting at 60° C. with 30 minutes of ultraviolet ray irradiation while changing rotating speed of the spin coater (data are shown as ratios when the thickness of the central portion of the lens is defined as 1).

TABLE 1

| Rotation speed | Central portion of the lens | Outermost peripheral of the lens |
| --- | --- | --- |
| 50 rpm | 1 | 0.632 |
| 100 rpm | 1 | 0.912 |
| 200 rpm | i | 1.000 |
| 300 rpm | 1 | 2.196 |

It is evident from the above results that a lens having almost uniform thickness can be molded by setting the rotating speed to about 100 to 200 rpm, a lens having thick peripheral portion can be obtained by carrying out the spin casting at a rotating speed of about 300 rpm or more and a lens having thick central portion can be obtained at a rotating speed of about 100 rpm or less. Though thickness of the material to be worn on the eyeball varies depending on each use, it may be about 0.03 to 5 mm, preferably about 0.05 to 0.5 mm, as average film thickness.

In consequence, diameter (lens size) and base curve (radius of curvature outside the lens) are determined by the depressed portion of the mold, and radius of curvature inside the lens is determined by the above-described solution characteristics, rotating speed, base curve of the mold and the like.

Though optimum ranges of the diameter and the base curve vary depending on the subjects to be applied (patients and the like), the diameter may be generally about 5 to 20 mm, and the base curve may be generally about 6 to 9 mm, preferably about 7 to 8.5 mm. The material of the mold may be selected generally from plastics (polybutylene terephthalate for example), glass, metals and the like, though other materials can also be used provided that they have a smooth surface and can be processed easily.

After completion of the molding, crosslinking is effected on the mold or after separating from the mold, by irradiating a light (preferably an ultraviolet ray having a wave length of approximately from 260 to 400 nm, more preferably approximately from 290 to 400 nm) for such a period of time as to obtain a gelation ratio in conformity with the purposes as described above. When the crosslinking is carried out on the mold, the crosslinked product is allowed to soak and swell in purified water, physiological saline, a buffer, a physiologically active compound-containing solution or the like and then detached from the mold.

Preferably, production of the material of the present invention to be worn on the eyeball may be carried out automatically in a sterilized atmosphere.

The material of the present invention to be worn on the eyeball includes not only those which have a single layer structure made of a single raw material but also those having a multilayer structure. In other words, it is possible to give the material both advantages of HCL and SCL to some degree by using a hard photocured crosslinked-glycosaminoglycan as a base material and coating the ophthalmic tissue-contacting surface of the hard base with a thin film of a flexible raw material. For example, two different photoreactive glycosaminoglycans (a high DS raw material and a low DS raw material) are used respectively as the base material and the thin film. When a solution of the low DS raw material is coated to the surface of the high DS raw material molded by the above-described casting method and then subjected to light irradiation after drying, if necessary, a photocuring and crosslinking reaction occurs in the base portion, in the thin film portion and their interface portions to give integral molding of a material to be worn on the eyeball, which has a three layer structure in which the inside and outside surfaces of the base portion are coated with thin films. It is possible also to mold a double layer material to be worn on the eyeball in which only the corneal tissue-contacting inside surface is coated with a thin film. The thin film portion becomes highly water-absorbable and forms flexible contacting surface having excellent compatibility with the ophthalmic tissue, while the base portion ensures hardness and mechanical strength because of its low water absorption and functions as an optically stable lens. Methods for the production of the multilayer material to be worn on the eyeball are not limited to the above. It may be obtained, for example, by a method comprising a first step in which a photocured crosslinked-glycosaminoglycan is formed as described above, a second step in which photocurable and crosslinkable group-bonded glycosaminoglycan is provided thereon followed by photocuring and crosslinking reaction and, if necessary, third or more additional steps which are effected in the same manner as the second step.

[Physical properties]

Basic physical properties required for the material of the present invention to be worn on the eyeball are as follows.

(1) Transparency

It is sufficient to have such a degree of transparency that the field of vision is not spoiled.

A percent optical transmittance is preferably about 50% or more at wavelength of 550 nm, especially about 90% or more when a colorless and transparent lens is expected. In some cases, photoirradiation to a photoreactive group-bonded glycosaminoglycan will cause a slight coloring due to oxidation and the like side reactions. When such a coloring becomes a problem, it can be prevented by increasing the irradiation intensity or reducing the irradiation time.

Alternatively, coloring may be effected positively using pigments, dyes and the like. In this case, the optical transmittance will be reduced.

The term "optical transmittance" as used herein means a value obtained by measuring visible light transmittance at the above-described wave length at room temperature using a spectrophotometer (Ubest-30, manufactured by Jasco).

(2) Gelation ratio sufficient to keep the shape for required period

Preferably, a photocured crosslinked-glycosaminoglycan has a gelation ratio of about 50% or more, especially about 80% or more when the material to be worn on the eyeball is used for the correction of visual acuity.

(3) Surface physical compatibility (high water wettability of the material surface)

Preferably, the material surface has a receding water contact angle of about 20 to 50° and an advancing water contact angle of about 20 to 70°. Optimum receding water contact angle is approximately 30 to 40°. Inside surface roughness can be controlled to a desired level, for example, by adjusting surface roughness of the mold.

The contact angle and surface roughness can be used as indices for the control of cell adhesion.

According to the present invention, the receding and advancing water contact angles are values determined by water droplet titration with a contact angle meter (CA-D, manufactured by Kyowa) using a film of the same raw material as the material to be worn on the eyeball.

(4) Biocompatibility with ophthalmic tissue (non-irritation against ophthalmic tissue)

It is desirable that bulbar conjuncta hyperemia, superficial keratitis, corneal erosion and the like symptoms in the front surface of the eye do not occur after at least one week-continuous wearing.

(5) Shape compatibility

The lens has a semi-spherical shape which is compatible in shape with the eye of mammals.

A CL type to be kept on the cornea can be stably worn on the eye when the material to be worn on the eyeball has a base curve more larger than the corneal curvature radius of the eyeball to be applied. The base curve may be preferably about 6 to 9 mm, more preferably about 7 to 8.5 mm.

Since the cornea is aspheric ellipsoid, the semi-spherical material to be worn on the eyeball is kept by the surface tension of tear fluid filled in the gap between the cornea and the material. In consequence, it is necessary to allow the material to move on the cornea within a certain range with the upper eyelid movement by each blink. Such a moving range may be generally about 1 to 5 mm, preferably about 2 to 3 mm, though it varies depending on the use of the material to be worn on the eyeball.

Alternatively, the material may have a semilunar or elliptic shape with a proper size so that it can be inserted inside the lower eyelid easily and is applicable to the shape of the inserted portion of the eyeball. Its size may be 4 to 10 mm in the major axis direction and 2 to 5 mm in the minor axis direction. Such a material is not expected to have a refraction correction effect or cornea protective effect but used as a base material for the controlled release of various drugs contained therein.

(6) Moisture content

The moisture content is generally about 5 to 80%, but its preferred range varies depending on the use. It may be about 5 to 30% in the case of a relatively hard HCL type material, and the moisture content is further increased in the case of a flexible SCL type material. As the moisture content increases, linear swelling ratio increases and dimentional stability, strength and refractive index decrease, so that the visual acuity correction effect decreases but the tissue compatibility is improved. In consequence, the moisture content may be adjusted to a relatively low level when the material is used as CL for visual acuity correction, and to a relatively high level when used for the medical treatment.

The moisture content is calculated by measuring weights of the material to be worn on the eyeball at room temperature, after equilibrium water absorption (Ww) and before swelling (Wd), and multiplying the resulting (Ww−Wd)/Ww by 100. Also, the water absorption can be represented by 100×(Ww−Wd)/Wd. A moisture content of 5% corresponds to water absorption of 5.2%, and a moisture content of 80% corresponds to water absorption of 400%.

(7) Oxygen permeability

The material of the present invention to be worn on the eyeball does not cause corneal erosion and the like serious symptoms in the front surface of the eye even after one week of its continuous wearing, thus showing excellent oxygen permeability of the material. The oxygen permeability can be improved by increasing moisture content of the material or reducing its thickness, especially at its central portion.

(8) Dimentional stability (Shape stability)

It is desirable that the material of the present invention has such a dimentional stability that its shape is not changed by autoclaving.

Since the dimentional stability varies depending on DS, light irradiation conditions, gelation ratio, water content and the like as described above, these conditions are optimized according to each purpose.

The range of linear swelling ratio as an index of the dimentional stability varies depending on each purpose, but is approximately from 1 to 40% in general. Particularly, it may be approximately from 1 to 10%, preferably from about 2 to 5% in the case of a relatively hard product, and approximately from 10 to 40%, preferably from about 15 to 35% in the case of a relatively soft product.

In this case, the linear swelling ratio is calculated by measuring diameters, after equilibrium water absorption (Dw) and before swelling (Dd), of a film of the same raw material as that of the material to be worn on the eyeball and multiplying the resulting (Dw−Dd)/Dd by 100.

(9) Refractive index

Though a specified refractive index is not always required when the material to be worn on the eyeball is used for a medical treatment purpose, it is desirable that the material has a refractive index similar to that of the usually used CL for visual acuity correction purpose when it is used for the correction of visual acuity. The index may be generally about 1.3 to 1.6, preferably about 1.4 to 1.5.

In this case, the refractive index is a value obtained by measuring a film of the same raw material as that of the material to be worn on the eyeball, after its equilibrium water absorption, using Abbe's refractometer (IT, manufactured by Atago) using a white light and under conditions of 20° C.

[Use]

<Visual Acuity Correction Use (refraction correction use)>

The material of the present invention to be worn on the eyeball can be used for the correction of visual acuity (correction of refraction) in the same manner as the case of conventional CL. That is, it can be used for the correction of astigmatism, myopia, hyperopia and the like. Especially, the material is useful for the correction of astigmatism when it has an intermediate hardness between those of the conventionally used HCL and SCL.

<Medical Treatment Use>

The photocured crosslinked-glycosaminoglycan, especially photocured crosslinked-HA, shows actions and effects as the basic characteristics of glycosaminoglycans, such as tissue non-adhesiveness, biodegradability, moisturizing effect (water keeping effect), corneal epithelium wound healing enhancing effect (corneal epithelium extension-enhancing effect) and the like (see JP-A 1-238530 regarding such actions of HA), and is possessed of a controlled release effect to release a physiologically active compound (compound having pharmacological effects; drug) included in the raw material at a constant releasing rate for a predetermined period of time. Because of such actions and effects, it can be used for various therapeutic purposes such as treatment of corneal damage and corneal ulcer, protection of the cornea after surgical operation, administration of drugs into the eye and transmucosal administration of drugs into the body.

Illustrative examples of the use of the material of the present invention include: healing enhancement of corneal epithelium disorders such as punctate stain (KSD), delayed corneal epithelium deficiency, corneal ulcer and the like; enhancement of corneal wound healing after surgical operation of refraction correction, cataract, ophthalmic wound, glaucoma and the like; relief of symptoms of tear secretion deficiency; and controlled release of such drugs included in the material as hyaluronic acid (uncrosslinked, unmodified), antiviral agents (acyclovir, idoxuridine, 5-bromovinylarabinofuranosyl uracil, adenine arabinoside, poly IC and the like), antibiotics (kanamycin, bekanamycin, amikacin, gentamicin, micronomicin, chloramphenicol, colistin, polymyxin B and the like), antifungal agents (amphotericin B, miconazole and the like), antiprotozoan drugs, antiglaucoma agents (timolol, β-adrenergic blocking drug and the like), antiinflammatory drugs, steroids, antihistaminics, miotics, anticholinergics, mydriatics, deconjestants or hormones (insulin, glucagon and the like) (for illustrative examples, see JP-A 1-238530, JP-A 1-279836, JP-W 61-501729, JP-A 4-230636 and JP-A 5-93889).

BEST MODE FOR CARRYING OUT THE INVENTION

The following examples are provided to further illustrate the present invention, but are not to be construed to limit the scope of the invention.

Experimental Example 1

Two types of cinnamic acid-bonded HA respectively having DS values of 1.7 and 2.9 were synthesized by esterification reaction of HA (molecular weight, 880,000) tri-n-butylamine salt with cinnamic acid chloride in a DMF solvent system in the presence of a base of pyridine as follows.

After the addition of anhydrous pyridine (40 ml) to a solution of hyaluronic acid (molecular weight, 880,000) tri-n-butylamine salt in DMF(200 ml, content of HA ca. 1 g), 2.2 molar excess of cinnamoyl chroride to molar numbers of the hydroxyl group of HA was added to the solution with vigorous stirring at room temperature. Esterification reaction was allowed to proceed at 75° C. for 2 hours with well stirring After the reaction, the reaction mixture was concentrated in vacuo. The concentrated solution was added to ethanol saturated with sodium acetate (2 l). The resulting precipitate was filtered off, thoroughly washed with ethanol and dried in vacuo to give a cinnamic acid-bonded HA. Yield: 0.97 g DS: 1.7.

Cinnamic acid-bonded HA was prepared using the same materials and procedure as described above, except for the use of 3.0 molar excess of cinnamoyl chloride to molar numbers of the hydroxyl group of HA. Yield: 1.20 g DS: 2.9.

The DMF solution of each cinnamic acid-bonded HA (100 mg/ml) was cast on a cover glass of 15 mm in diameter. After drying, this was irradiated with an ultraviolet light of 290 nm or more (irradiation intensity, 0.26 mW/cm$^2$) for 30 minutes using a high pressure mercury lamp (H-400P, 400W, manufactured by Toshiba). Physical properties of the thus obtained photocured crosslinked- HA film (film thickness, about 0.08 mm) were observed. The observed results are shown in Table 2.

TABLE 2

| DS | 1.7 | 2.9 |
|---|---|---|
| Gelation ratio | 84 | 91 |
| Optical Transmittance (%) | 95 | 90 |
| Refractive index | 1.432 | 1.465 |
| Water content (%) | 11.3 | 8.4 |
| Linear Swelling Ratio (%) | 3.1 | 2.1 |
| Receding water contact angle (degree) | 32.2 | 40.1 |
| Advancing water contact angle (degree) | 57.0 | 65.6 |

These films were light yellow in color and transparent, and the photocured crosslinked-HA films having DS values of 1.7 and 2.9 showed visible light transmittances of 95% and 90%, respectively. Both films showed a low water content of about 8 to 11%. In comparison with the film of high DS value, the low DS film showed higher water content and linear swelling ratio and lower water contact angle.

Example 1

Figure 1B:
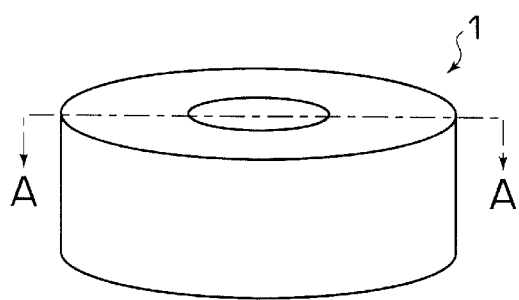
FIG. 1 shows a graph illustrating an example of the mold to be used for the preparation of the material to be worn on the eyeball of the present invention. In the drawing, 1 represents a mold, 2 represents a base curve and 3 represents a depressed portion.
Figure 1A:
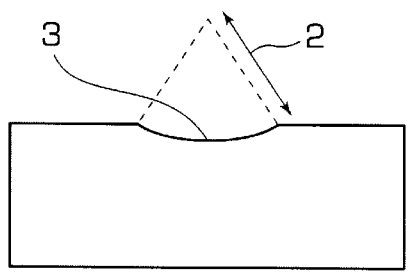
Figure 1C:
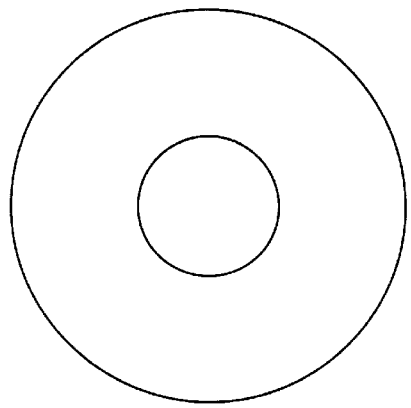

The mold shown in FIG. 1 was charged with 70 μl of the DMF solution (100 mg/ml) of each cinnamic acid-bonded HA synthesized in Experimental Example 1, placed in a spin coater (1H-DXII, manufactured by-Mikasa) and then subjected to spin casting at a rotating speed of 100 rpm and at a temperature of 60° C. After 30 minutes of photoirradiation carried out in the same manner as described in Experimental Example 1, the thus crosslinked lens-shaped film was soaked and swelled in distilled water and then released from the mold to obtain a CL sample made of each photocured crosslinked-HA. In this manner, prepared were three CL samples having base curves of about 7.6 mm, about 7.9 mm and about 8.2 mm in diameter, and having a lens size of about 8.8 mm and a central portion thickness of about 0.1 mm, respectively.

Example 2

Corneas of total of 6 eyes of 3 colored rabbits were checked for their radius of curvature (average value) using a corneal shape analyzer (coroneal analysis system; eye sys, manufactured by Nidek), and their corneal thickness using an ultrasonic corneal thickness meter (Optical echopachymeter; Echo Scan, US-2000, manufactured by Nidek). The CL made from a cinnamic acid-bonded HA of 1.7 in DS value prepared in Example 1 was soaked in physiological saline, autoclaved for 30 minutes and then worn on the right eye of each rabbit(present invention), while its left eye was worn with a continuously wearable commercial oxygen permeable HCL (GPHCL) (Menicon $O_2$, manufactured by Toyo Contact Lens) as a control (see Table 3). After 1 week of continuous wearing during which slit-lamp inspection was carried out at intervals, the lenses were released to measure corneal thicknesses. The observed results are shown in Table 3. Thereafter, the rabbits were sacrificed by intravenous anesthesia with excess pentobarbital to prepare corneal tissue specimens.

TABLE 3

| Rabbit No. | Eye | Rabbit cornea Radius of curvature (mm) | Thickness (µm) | CL Type | Base curve (mm) | Corneal thickening ratio (%) |
|---|---|---|---|---|---|---|
| 1 | right | 7.39 | 407 | present invention | 7.60 | 8.85 |
|   | left  | 7.18 | 397 | GPHCL | 7.20 | 8.82 |
| 2 | right | 7.32 | 404 | present invention | 7.60 | 5.94 |
|   | left  | 7.26 | 405 | GPHCL | 7.30 | 6.67 |
| 3 | right | 7.62 | 396 | present invention | 7.90 | 4.04 |
|   | left  | 7.45 | 401 | GPHCL | 7.50 | 4.74 |

As is evident from the results shown in Table 3, when the CL of the present invention having a base curve larger than the measured value of corneal curvature radius is worn, it can be held on the eyeball stably. In addition, movement of each CL due to blinking was within the range of from 2 to 3 mm. Bulbar conjunctiva hyperemia, superficial keratitis and the like symptoms in the front surface of the eye were not observed during the test period of continuous wearing. After one week of the continuous wearing, the corneal thickness was increased by a factor of 6.28% in average in the group of present invention, and 6.74% in average in the control group, in comparison with the thickness before wearing, but there was no significant difference between these two groups. In this instance, the corneal thickening ratio was defined as 100× (corneal thickness after wearing-corneal thickness before wearing)/(corneal thickness before wearing). No problematic findings were obtained by histological examination of the corneal specimens obtained after 1 week of continuous wearing in both groups. In other words, the lens of the present invention has an oxygen permeability equal to or higher than that of the control.

INDUSTRIAL APPLICABILITY

The present invention provides semi-spherical materials to be worn on the eyeball for use in various purposes such as contact lenses for visual acuity correction or medical treatment use, cornea protecting materials, controlled drug release contact lenses and the like, which comprise, as a main component, a crosslinked product of a glycosaminoglycan existing in the living body as an extracellular matrix component of connective tissues, to which photoreactive groups are bonded, wherein various requirements such as dimentional stability, transparency, surface water wettability, tissue compatibility, oxygen permeability and the like can be satisfied by optionally selecting DS value, crosslinking density and the like.

We claim:

1. A material to be worn on a mammalian eyeball, wherein said material has a shape of a semi-spherical surface that is compatible in shape with a mammalian eyeball, wherein said shape results from either cutting of a part of a spherical surface or cutting of a part of a spherical surface on which holes, notches, or slots are partly arranged, and wherein said material has biological and surface-physical compatibilities with ophthalmic tissues and comprises, as a main component, a substantially transparent photocured crosslinked-glycosaminoglycan obtained by allowing photoreactive groups covalently bonded to a glycosaminoglycan to crosslink with each other upon irradiation, wherein said photoreactive groups covalently bonded to the glycosaminoglycan are an acyl group of cinnamic acid or a derivative of cinnamic acid, an acyl group of 1-carboxyalkylthymine or an acyl group of 7-coumaryloxyacetic acid.

2. The material to be worn on the eyeball according to claim 1 wherein said glycosaminoglycan is hyaluronic acid or chondroitin sulfate.

3. The material to be worn on the eyeball according to claim 1 wherein the material surface has high water wettability.

4. The material to be worn on the eyeball according to claim 3 wherein said water wettability of material surface is defined as receding contact angle with water of about 20 to 50°.

5. The material to be worn on the eyeball according to claim 1 wherein gelation ratio of said photocured crosslinked-glycosaminoglycan is about 50% or more.

6. The material to be worn on the eyeball according to claim 1 wherein gelation ratio of said photocured crosslinked-glycosaminoglycan is about 80% or more.

7. The material to be worn on the eyeball according to claim 1 wherein said material has a characteristic as a contact lens for use in visual acuity correction.

8. The material to be worn on the eyeball according to claim 1 wherein diameter of the material is about 5 to 20 mm, and the base curve of the material is about 6 to 9 mm.

9. The material to be worn on the eyeball according to claim 1 wherein the range of linear swelling ratio of the material is approximately from 1 to 40%.

10. The material to be worn on the eyeball according to claim 1 wherein the range of refractive index of the material is about 1.3 to 1.6.

11. The material to be worn on the eyeball according to claim 1 wherein said photocured crosslinked-glycosaminoglycan has a multilayer structure having different crosslinking densities.

12. The material to be worn on the eyeball according to claim 1, wherein said material has a water wettability of material surface as receding contact angle with water of about 20 to 50°, has a refractive index of about 1.3 to 1.6, and has a gelation ratio of the photocured crosslinked-glycosaminoglycan being about 50% or more.

13. A method for manufacturing a material to be worn on a mammalian eyeball, wherein said material has a shape of a semi-spherical surface that is compatible in shape with a mammalian eyeball, wherein said shape results from either cutting of a part of a spherical surface or cutting of a part of a spherical surface on which holes, notches, or slots are partly arranged, and wherein said material has biological and surface-physical compatibilities with ophthalmic tissues, wherein said method comprises manufacturing said material from a composition which comprises, as a main component, a substantially transparent photocured crosslinked-glycosaminoglycan obtained by allowing photoreactive groups covalently bonded to a glycosaminoglycan to crosslink with each other upon irradiation, wherein said photoreactive groups covalently bonded to the glycosaminoglycan are an acyl group of cinnamic acid or a derivative of cinnamic acid, an acyl group of 1-carboxyalkvlthymine or an acyl group of 7-coumaryloxyacetic acid.

* * * * *